US011871896B2

(12) United States Patent
Nikolayev et al.

(10) Patent No.: US 11,871,896 B2
(45) Date of Patent: Jan. 16, 2024

(54) BIOTELEMETRY DEVICE THAT CAN BE INGESTED AND IMPLANTED IN VIVO

(71) Applicants: BODYCAP, Herouvile Saint Clair (FR); CENTRE NATIONAL DE LA RECHERCHE SCIENTIFIQUE, Paris (FR); UNIVERSITE DE RENNES 1, Rennes (FR)

(72) Inventors: Denys Nikolayev, Rennes (FR); Maxim Zhadobov, Betton (FR); Ronan Sauleau, Acigné (FR)

(73) Assignees: BODYCAP, Herouvile Saint Clair (FR); CENTRE NATIONAL DE LA RECHERCHE SCIENTIFIQUE, Paris (FR); UNIVERSITE DE RENNES, Rennes (FR)

( * ) Notice: Subject to any disclaimer, the term of this patent is extended or adjusted under 35 U.S.C. 154(b) by 814 days.

(21) Appl. No.: 16/764,302

(22) PCT Filed: Oct. 2, 2018

(86) PCT No.: PCT/FR2018/052418
§ 371 (c)(1),
(2) Date: May 14, 2020

(87) PCT Pub. No.: WO2019/069008
PCT Pub. Date: Apr. 11, 2019

(65) Prior Publication Data
US 2021/0030305 A1    Feb. 4, 2021

(30) Foreign Application Priority Data

Oct. 2, 2017   (FR) ........................................ 1759198

(51) Int. Cl.
*A61B 5/0538*    (2021.01)
*A61B 5/07*      (2006.01)

(52) U.S. Cl.
CPC .............. *A61B 5/0538* (2013.01); *A61B 5/07* (2013.01)

(58) Field of Classification Search
None
See application file for complete search history.

(56) References Cited

U.S. PATENT DOCUMENTS

| 6,061,589 A * | 5/2000 | Bridges ............... A61B 6/0435 600/430 |
| 2002/0077536 A1 * | 6/2002 | Diab .................. A61B 5/14546 600/323 |

(Continued)

OTHER PUBLICATIONS

International Search Report dated Jan. 23, 2019 for PCT application PCT/FR2018/052418.

(Continued)

*Primary Examiner* — Etsub D Berhanu
*Assistant Examiner* — Samuel C Kim

(57) ABSTRACT

The biotelemetry device (100) comprises a microcontroller (101) for generating an electrical setpoint signal (CS); a radio antenna (103) for transmitting an electromagnetic wave (EMS) by converting an incident electrical signal (IS); a radiofrequency circuit (102), interconnected between the microcontroller (101) and the radio antenna (103). The radio antenna (103) is configured such that, when the biotelemetry device (100) is placed in the biological medium (110), it can be impedance-mismatched relative to the radiofrequency circuit (102) so as to generate a reflected electrical signal (RS) by reflecting a fraction of the incident electrical signal at the same time that the radio antenna is transmitting the electromagnetic wave (EMS).

15 Claims, 7 Drawing Sheets

(56) References Cited

U.S. PATENT DOCUMENTS

| | | | |
|---|---|---|---|
| 2004/0249258 A1* | 12/2004 | Tupin, Jr. | A61B 5/05 600/407 |
| 2008/0234574 A1* | 9/2008 | Hancock | A61B 18/1815 600/430 |
| 2010/0121318 A1* | 5/2010 | Hancock | A61B 5/0507 342/174 |
| 2010/0137686 A1 | 6/2010 | Meron et al. | |
| 2010/0168730 A1 | 7/2010 | Hancock et al. | |
| 2014/0107638 A1 | 4/2014 | Hancock et al. | |
| 2016/0073924 A1 | 3/2016 | Weinstein et al. | |
| 2017/0095667 A1 | 4/2017 | Yakovlev et al. | |

OTHER PUBLICATIONS

Blackham et al., "An Improved Technique for Perimittivity Measurements Using a Csaxial Probe", Oct. 1997, pp. 1093-1099, IEEE Transactions on Instrumentation and Measurement, vol. 46, No. 5.

Burdette et al., "In Vivo Probe Measurement Technique for Determining Dielectric Properties at VHF Through Microwave Frequencies", Apr. 1980, pp. 414-427, IEEE Transactions on Microwave Theory and Techniques, vol. MTr-28, No. 4.

Kiourti et al., "Implantable and Ingestible Medical Devices With Wireless Telemetry Functionalities: A Review of Current Status and Challenges", 2013, pp. 1-15, Bioelectromagnetics 35:1-15 (2014), Wiley Periodicals, Inc.

\* cited by examiner

|  | 404 MHz | | 434 MHz | | 915 MHz | | 2.4 GHz | | 24 GHz | | 60 GHz | |
|---|---|---|---|---|---|---|---|---|---|---|---|---|
|  | $\varepsilon_r$ | $\sigma$ | $\varepsilon_r$ | $\sigma$ | $\varepsilon_r$ | $\sigma$ | $\varepsilon_r$ | $\sigma$ | $\varepsilon_r$ | $\sigma$ | $\varepsilon_r$ | $\sigma$ |
| Stomach | 67.4 | 1.00 | 67.2 | 1.01 | 65.0 | 1.19 | 62.2 | 2.17 | 29.9 | 35.1 | 13.4 | 60.0 |
| Small Intestine | 66.0 | 1.90 | 65.3 | 1.92 | 59.4 | 2.17 | 54.5 | 3.13 | 25.8 | 31.0 | 12.0 | 52.0 |
| Colon | 62.5 | 0.86 | 62.0 | 0.87 | 57.9 | 1.09 | 54.0 | 2.00 | 25.8 | 29.8 | 12.0 | 50.7 |
| Muscle | 57.1 | 0.80 | 56.9 | 0.80 | 55.0 | 0.95 | 52.8 | 1.71 | 27.4 | 29.4 | 12.9 | 52.8 |

FIG.5

BIOTELEMETRY DEVICE THAT CAN BE INGESTED AND IMPLANTED IN VIVO

CROSS-REFERENCE TO RELATED APPLICATION

This application is a national stage application, filed under 35 U.S.C. § 371, of International Patent Application No. PCT/FR2018/052418, filed on Oct. 2, 2018, which claims the priority of French application No. 1759198 filed Oct. 2, 2017, the contents of which are incorporated by reference.

TECHNICAL AREA

The present description relates to a biotelemetry device intended to be used in an in vivo medium and to an associated method.

STATE OF THE ART

In the biomedical field, biotelemetry devices are used for the acquisition of physiological signals and the analysis of associated physiological data.

Among the biotelemetry devices, there are ingestible and/or implantable wireless biotelemetry devices, which can be used both for the collection and the transmission of physiological signals and for the implementation of therapeutic functions, such as for example the delivery of drugs or electrical stimulation. These biotelemetry devices are for example in the form of ingestible capsules or implants which can be inserted into the body of humans or animals.

The document entitled "*Implantable and ingestible medical devices with wireless telemetry functionalities: a review of current status and challenges*", by A. Kiourti et al, published in the journal "Bioelectromagnetics" in 2014, presents an overview of devices that can be ingested and/or implantable in vivo.

These biotelemetry devices incorporate at least one radio antenna for transmitting data to external equipment for controlling/analyzing data or for receiving commands from such equipment. This external equipment is used in particular to analyze ex vivo the data transmitted by the radio antenna.

By "external", here, we therefore refer to equipment external to the biological environment in which the biotelemetry device has been implanted or ingested. For example, for a human or animal body, the biotelemetry device is said to be external to the human or animal body.

These biotelemetry devices can integrate one or more miniaturized sensors or transducers for the measurement of physiological variables originating from the surrounding medium, for example a sensor capable of measuring pH, temperature or pressure throughout the gastrointestinal tract. pH detection sensors, produced in the form of glass electrodes, are however bulky, expensive and consume energy.

Due to their reduced size, biotelemetry devices intended to be used in an in vivo medium imply constraints as to the choice, the arrangement and the number of usable electronic components.

There thus appears a need for a biotelemetric device, usable in vivo, for example ingestible or implantable in vivo, simplified, with consumption and reduced cost.

SUMMARY

The present description relates, according to a first aspect, to a biotelemetry device for use in a biological medium. This device comprises: a microcontroller configured to generate an electrical setpoint signal; a radio antenna configured to transmit an electromagnetic wave by converting an incident electrical signal; a radiofrequency circuit, interconnected between the microcontroller and the radio antenna. The radio antenna is configured to, when the biotelemetry device is placed in the biological medium, be impedance mismatched with respect to the radiofrequency circuit so as to generate a reflected electrical signal by reflection of a fraction of the incident electrical signal at the same time as the radio antenna emits the electromagnetic wave. The radiofrequency circuit is configured to pick up a first fraction of the electrical setpoint signal, transmit to the radio antenna a second fraction of the electrical setpoint signal forming the incident electrical signal and pick up the electrical signal reflected by the radio antenna. The microcontroller is configured to determine, relative to the first fraction of the electrical setpoint signal, a reflection coefficient corresponding to the fraction of the electrical signal reflected by the radio antenna.

In the device according to the first aspect, the radio antenna is used concomitantly for the emission of electromagnetic waves, detectable for example by an external equipment, and to produce a reflected electrical signal resulting from a mismatch of impedance of the radio antenna with respect to the radio frequency circuit.

Since the impedance of the radio antenna is highly dependent on the surrounding environment in which it is placed, the electrical signal reflected by the radio antenna is representative of the electromagnetic properties (including permittivity, conductivity) of the surrounding environment. The reflection coefficient can therefore be used to characterize the electromagnetic properties of this surrounding medium.

Such a biotelemetry device thus makes it possible, from the reflection coefficient, to detect and quantify the variations in the electromagnetic properties (in particular permittivity, conductivity) of biological tissues and to deduce therefrom the physiological changes correlated with the variation of the electromagnetic properties. The calculation of the reflection coefficient, as well as the determination of the electromagnetic properties on the basis of the reflection coefficient, can be carried out by the microcontroller or else by the external equipment communicating with the microcontroller by means of the electromagnetic waves emitted by the radioelectric antenna.

The combination of this method of detecting the electromagnetic properties of biological tissues with an additional sensor such as a temperature sensor makes it possible to determine physiological parameters, such as pH, glucose level, lactate level, cholesterol level, and without requiring a specific sensor for each of these physiological parameters. Consequently, it is possible to reduce the size of the biotelemetry device compared to devices incorporating such specific sensors or else to use the interior space of the biotelemetry device to integrate other components. One can for example use the biotelemetry device to realize a non-invasive and autonomous glucose sensor, capable of automatically alerting the patient or his doctor in case of abnormal glucose level.

The biotelemetry device described in this document is more energy efficient and less costly than devices with dedicated biomedical sensors or application circuits. In addition, the biotelemetry device makes it possible to measure in vivo the EM properties of an organ of the human or animal body, which has not yet been achieved to date.

The combination of this technique for detecting the electromagnetic properties of biological tissues with devices such as wireless endoscopic capsules or drug delivery systems makes it possible to activate these devices or to deliver a drug when the electromagnetic properties of the medium correspond to values of interest.

In one or more embodiments of the biotelemetry device according to the first aspect, the microcontroller is further configured to obtain a first electrical comparison signal resulting from a comparison between a reference signal and the first fraction picked up from the signal of the electrical setpoint signal and to obtain a second electrical comparison signal resulting from a comparison between the reference signal and the electrical signal reflected by the radio antenna.

In one or more embodiments of the biotelemetry device according to the first aspect, the microcontroller is further configured to determine the reflection coefficient from the first electrical comparison signal and the second electrical comparison signal.

In one or more embodiments of the biotelemetry device according to the first aspect, the microcontroller is further configured to determine an electromagnetic parameter of the biological medium from the amplitude and the phase of the first electrical comparison signal and the amplitude and the phase of the second electrical comparison signal.

In one or more embodiments of the biotelemetry device according to the first aspect, the radiofrequency circuit comprises a power divider configured to pick up the first fraction of the electrical setpoint signal and generate the incident electrical signal.

In one or more embodiments of the biotelemetry device according to the first aspect, the radiofrequency circuit comprises a directional coupler configured to pick up the electrical signal reflected by the radio antenna.

In one or more embodiments of the biotelemetry device according to the first aspect, the radio frequency circuit comprises a reference receiver configured to compare the reference signal and the first fraction picked up from the signal of the electrical setpoint signal and a test receiver configured for compare the reference signal and the electrical signal reflected by the radio antenna.

In one or more embodiments of the biotelemetry device according to the first aspect, the radio frequency circuit further comprises at least one switch configured to switch the radiofrequency circuit from a first operating mode to a second operating mode and vice versa, the radiofrequency circuit being configured for, in the first operating mode, for picking up the first fraction of the setpoint electrical signal and the fraction of the electrical signal reflected by the radio antenna and for generating the incident electrical signal from the second fraction of the electrical setpoint signal; the radio frequency circuit being configured to, in the second operating mode, transmit the entire electrical setpoint signal to the radio antenna and pick no fraction of the electric signal reflected by the radio antenna up.

In one or more embodiments, the biotelemetry device according to the first aspect, comprises an impedance matching circuit, interconnected between the microcontroller and the radiofrequency circuit and configured to implement an impedance matching parametered as a function of the determined reflection coefficient.

In one or more embodiments, the reflection coefficient is, at the operating frequency of the radio antenna, less than −3 dB.

In one or more embodiments, the microcontroller is further configured to determine from the reflection coefficient a complex impedance of the antenna in the biological medium at the operating frequency of the radio antenna.

In one or more embodiments, the microcontroller is further configured to determine one or more electromagnetic properties of the biological medium from a model linking the complex impedance of the antenna in free space to the complex impedance of the antenna in the biological environment and the electromagnetic properties.

According to another aspect, the invention relates to a system comprising a biotelemetry device and an external device configured to receive electromagnetic waves emitted by the antenna of the biotelemetry device and/or send commands to the biotelemetry device.

In one or more embodiments, the external device is further configured to determine from the reflection coefficient a complex impedance of the antenna in the biological medium at the operating frequency of the radio antenna and to determine electromagnetic properties of the biological medium from a model linking the complex impedance of the antenna in free space to the complex impedance of the antenna in the biological medium and the electromagnetic properties.

The characteristics of the various embodiments of the biotelemetry device according to the first aspect can be combined with one another.

The present description also relates, according to a second aspect, to a biotelemetry measurement method, the method being intended to be implemented by means of a biotelemetry device placed in a surrounding biological medium, the method comprising a generation of a electrical setpoint signal by a microcontroller of the biotelemetry device; an emission, by a radio antenna of the biotelemetry device, of an electromagnetic wave by conversion of the incident electrical signal; a generation of a reflected electrical signal, the reflected electrical signal resulting from an impedance mismatch of the radio antenna with respect to the radiofrequency circuit when the biotelemetry device is placed in the biological medium and being generated by reflection by the radio antenna of a fraction of the incident electric signal concomitantly with the emission of the electromagnetic wave; a picking up, by a radiofrequency circuit of the biotelemetry device, interconnected between the microcontroller and the radio antenna, of a first fraction of the electrical setpoint signal and of the electric signal reflected by the radio antenna; a transmission to the radio antenna of a second fraction of the setpoint electrical signal forming the incident electrical signal; a determination, by the microcontroller, relative to the first fraction of the setpoint electrical signal, of a reflection coefficient corresponding to the fraction of the electrical signal reflected by the radio antenna.

According to one or more embodiments, the method according to the second aspect is implemented by the biotelemetry device according to the first aspect. Thus, the biotelemetry device according to the first aspect comprises means for implementing the method according to the second aspect and, conversely, the method according to the second aspect comprises steps corresponding to the functions implemented by the biotelemetry device according to the first aspect. The characteristics, properties, advantages and/or effects of the biotelemetry device according to the first aspect can be directly transposed to the method according to the second aspect and vice versa.

BRIEF DESCRIPTION OF THE FIGS.

Other advantages and characteristics of the technology presented above will appear on reading the detailed description below, made with reference to FIGS. in which:

FIG. 1 schematically represents a biotelemetric device according to an exemplary embodiment;

FIG. 2 schematically represents a biotelemetric device according to an exemplary embodiment and an external device communicating with the biotelemetric device via a radio connection;

FIGS. 3A and 3B schematically represent an example of installation of a biotelemetry device;

FIG. 5 illustrates the relationship between the electromagnetic properties of a medium and the operating frequency of a biotelemetry device according to an exemplary embodiment.

In the various embodiments which will be described with reference to FIGS., Similar or identical elements have the same references.

DETAILED DESCRIPTION

The various embodiments and aspects described below can be combined or simplified in many ways.

Only certain embodiments of examples are described in detail to ensure the clarity of the description, but these examples are not intended to limit the general scope of the principles emerging from this description considered as a whole.

Figure 1:
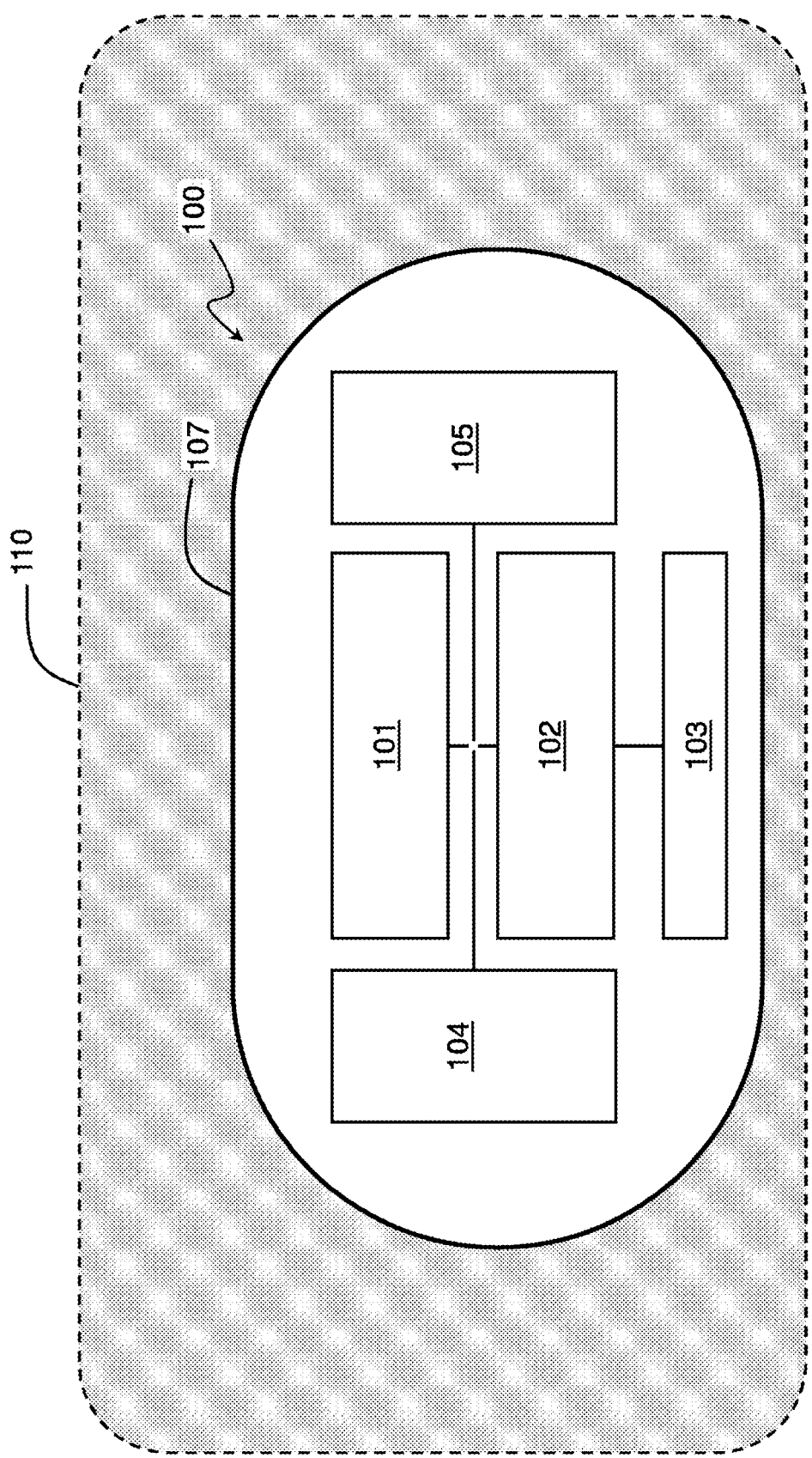

FIG. 1 schematically shows an example of a biotelemetry device 100, in the form of an ingestible capsule.

The biotelemetry device 100 comprises a microcontroller 101, a radio frequency circuit 102, a wireless communication unit 103, a power source 104. Optionally, the biotelemetry device 100 may include an additional circuit 105, for example a biomedical application circuit or a sensor.

In one or more embodiments, the biotelemetry device 100 can be produced by means of one or more integrated circuits, each integrating one or more of the components of the biotelemetry device 100.

In one or more embodiments, the power source 104 is configured to electrically power the microcontroller 101, the radio frequency circuit 102, the wireless communication unit 103 and the additional circuit 105.

In one or more embodiments, the wireless communication unit 103 is configured to communicate via a radio connection with an external device. The wireless communication unit 103 can for example transmit data (for example biotelemetry data acquired by the biotelemetry device 100) to the external device and receive data (for example operational instructions and/or therapeutic treatment) from such an external device.

In one or more embodiments, the wireless communication unit 103 is produced in the form of a radio antenna capable of transmitting and receiving electromagnetic waves at high frequencies, for example in the range from $10^7$ Hz to $10^{10}$ Hz. The antenna can be made of electrically conductive material (for example, metal such as copper, aluminum, silver, or an alloy, etc.). The antenna can be printed on a substrate of dielectric material. According to another exemplary embodiment, the wireless communication unit 103 is produced in the form of an inductive coil for transmitting and receiving data by a near field technique.

In one or more embodiments, the microcontroller 101 is configured to process data, for example to process the data received by the wireless communication unit 103 or data acquired by the additional circuit 105.

All the components of the biotelemetry device 100 (the microcontroller 101, the radio frequency circuit 102, the wireless communication unit 103, the power source 104 and optionally, the an additional circuit 105) is integrated in a biocompatible capsule 107. The capsule can for example be made of biocompatible plastic material (PVC, PTFE, PEEK, Polyethylene etc.), polymer or ceramic.

In one or more embodiments, the radio frequency circuit 102 is interconnected between the microcontroller 101 and the radio antenna 103. The radio frequency circuit 102 serves as an electrical interface between the microcontroller 101.

In one or more embodiments, the biomedical application circuit 105 is configured to implement diagnostic functions and/or therapeutic functions. The diagnostic functions may include functions for acquiring or measuring diagnostic data, for example by means of one or more sensors, such as for example, temperature sensors, electronic sensors, MEMS ("Microelectromechanical Systems") or sensors microfluidics. Diagnostic functions may include endoscopy, image acquisition, measurement of glucose or other physiological parameters, antibody detection, etc. Therapeutic functions can include, for example, drug delivery and electrical stimulation, such as nerve stimulation.

The biotelemetry device 100 is intended to be used in a surrounding biological medium 110, for example after ingestion or implantation in vivo. As the biotelemetry device 100 moves through the human body, for example during gastrointestinal transit, this biological medium 110 is likely to have various properties.

The electromagnetic (EM) properties of the biological medium 110 surrounding the biotelemetry device 100 determines the coupling between the radio antenna 103 and the biological medium 110 and the absorption of EM fields by this biological medium 110. Knowing these EM properties makes it possible to adapt the configuration of the radio antenna 103 to optimize the wireless transmission performance of the radio antenna 103 through the biological medium. In particular, the coupling between the radio antenna 103 and the biological medium 110 is important, and the transmission properties of the radio antenna are affected by variations in the EM properties of the biological medium 110 in which the biotelemetry device 100 is located. This variation in the EM properties of the biological medium 110 can therefore be detected and, if necessary, quantified.

Figure 2:
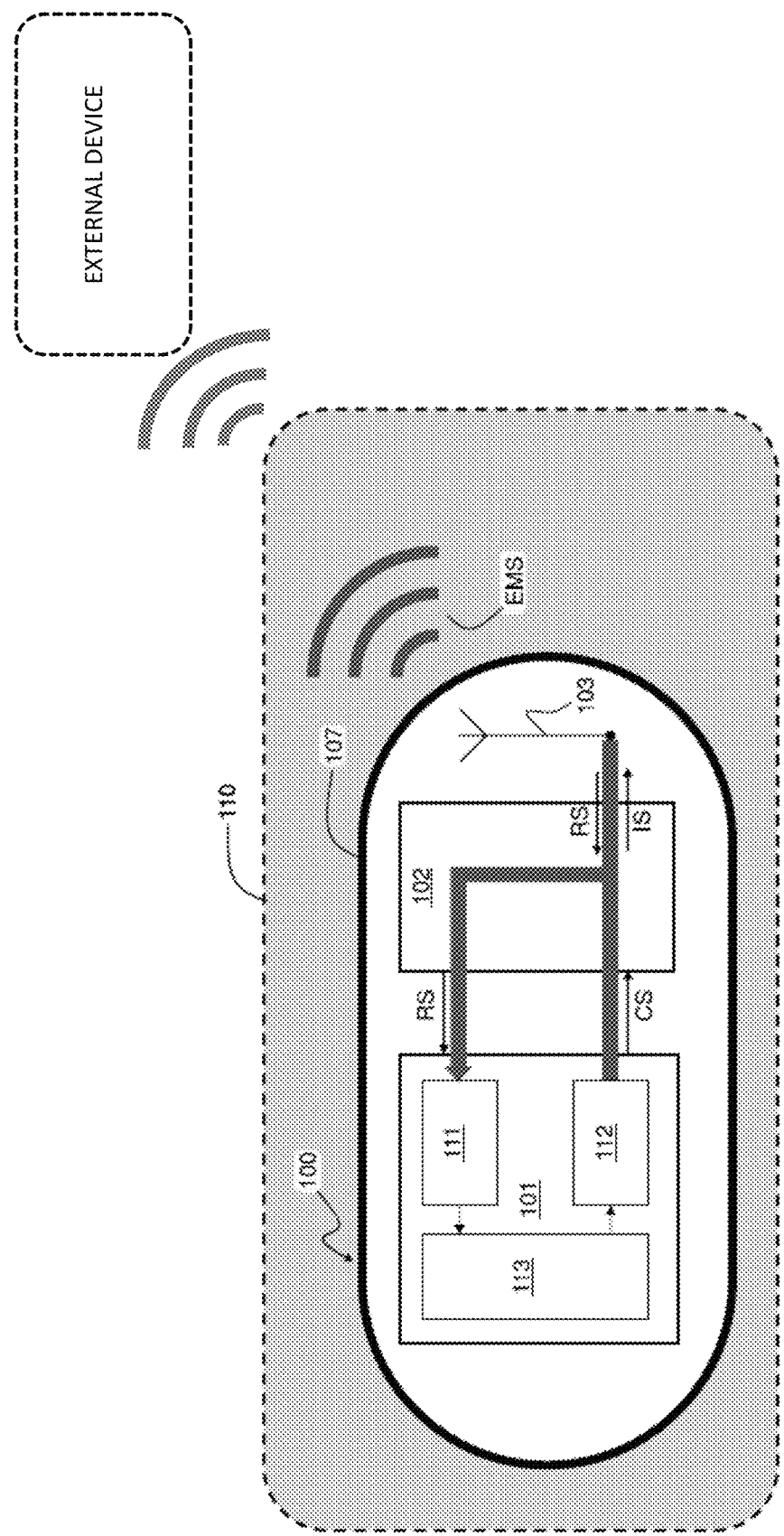

FIG. 2 illustrates in more detail the operating principle of the biotelemetry device 100.

According to one or more embodiments, the microcontroller 101 is configured to generate an electrical setpoint signal CS to be converted into an electromagnetic wave EMS by the radio antenna 103.

The radio antenna 103 is configured to transmit an EMS electromagnetic wave by conversion of an incident electrical signal IS. According to one or more embodiments, the incident electrical signal IS is generated by the radio frequency circuit 102 from the electrical setpoint signal CS.

According to one or more embodiments, the radio antenna 103 is configured to, when the biotelemetry device 100 is placed in the biological medium 110, be impedance mismatched with respect to the radio frequency circuit 102 so as to generate a reflected electrical signal RS by reflection of a fraction of the incident electrical signal IS, at the same time as the radio antenna 103 emits an electromagnetic wave EMS.

The electrical signal RS reflected by the radio antenna 103 is a function of the impedance mismatch rate between the radio antenna 103 and the radio frequency circuit. However, the impedance of the radio antenna 103 strongly depends on the EM properties of the biological medium 110 with which the radio antenna 103 is coupled. Thus, the electrical signal RS reflected by the radio antenna 103 is a function of the EM properties of this biological medium 110.

The complex in vivo impedance of the radio antenna 103 is noted:

$$Z_{ANT}(\omega, \hat{\varepsilon}) = R + jX \quad \text{(eq1)}$$

This complex impedance $Z_{ANT}(\omega, \hat{\varepsilon})$ depends on the angular frequency ω, expressed in rad/s (ω=2πf$_0$, f$_0$ being the operating frequency of the radio antenna 103) and on the complex permittivity $\hat{\varepsilon} = \varepsilon - j\ddot{\varepsilon}$ of surrounding biological medium 110, where the real part $\dot{\varepsilon} = \varepsilon_r \varepsilon_0$ is the permittivity of the biological medium, $\varepsilon_r$ being the relative permittivity, and the imaginary part $\ddot{\varepsilon} = \varepsilon/\omega$ representing the losses due to the conductivity σ (expressed in S/m) of the biological medium with respect to the angular frequency ω.

Given the non-magnetic properties (i.e., having a magnetic permeability μ=μ$_0$ equal to that of free space) of the surrounding biological medium 110, the complex impedance $Z_{ANT}(n\omega, \varepsilon_0)$ of the radio antenna in free space is linked to its complex impedance in vivo $Z_{ANT}(\omega, \hat{\varepsilon})$ by the relation:

$$\frac{Z_{ANT}(\omega, \hat{\varepsilon})}{\eta} = \frac{Z_{ANT}(n\omega, \varepsilon_0)}{\eta_0} \quad \text{(eq 2)}$$

where η is the intrinsic complex impedance of the biological medium, η$_0$ is the intrinsic impedance of free space and n is the refractive index of the biological medium compared to air. This relationship has been described for example by Burdette et al., in the article "In vivo Probe Measurement Technique for Determining Dielectric Properties at VHF through Microwave Frequencies", IEEE Transactions on Microwave Theory Technology, vol. 28, n° 4, pp 414-427, April 1980. This equation (eq2) applies to any type of radio antenna for any expression of the radio antenna impedance $Z_{ANT}(\omega, \hat{\varepsilon})$ in a dielectric medium and any expression of the radio antenna impedance $Z_{ANT}(n\omega, \varepsilon_0)$ in free space.

Since the reflected electrical signal RS by the radio antenna 103 depends on the EM properties (in particular, relative permittivity $\varepsilon_r$ and conductivity σ) of the biological medium 110 with which the radio antenna 103 is coupled, the radio antenna 103 can be used both for the emission of an electromagnetic wave EMS and to deduce therefrom the EM properties of the biological medium 110 from the electrical signal RS reflected by the radio antenna.

The impedance mismatch rate between the radio antenna and the radio frequency circuit can be evaluated on the basis of the reflection coefficient $S_{11}$. This reflection coefficient $S_{11}$ can be determined at the operating frequency of the radio antenna as a function of the incident electrical signal IS and the reflected electrical signal RS. This reflection coefficient $S_{11}$ is a function of the EM properties (in particular, permittivity and conductivity) of the biological medium 110 with which the radio antenna 103 is coupled.

According to one or more embodiments, the reflection coefficient $S_{11}$ is determined as the complex relationship (i.e. amplitude and phase) between the complex intensity of the incident electrical signal IS and the complex intensity of the reflected electrical signal RS:

$$S_{11} = E^{RS}/E^{IS} \quad \text{(eq3)}$$

where E represents the complex intensity of an electric field or signal.

This reflection coefficient $S_{11}$ is also related to the complex impedance $Z_{ANT}$ of the antenna and to the complex impedance $Z_{RF}$ of the radiofrequency circuit by the relation:
$S_{11} = (Z_{ANT} - Z_{RF})/(Z_{ANT} + Z_{RF})$ (eq. 4)

The complex impedance $Z_{ANT}(\omega, \hat{\varepsilon})$ of the antenna in vivo is itself linked to its impedance $Z_{ANT}(n\omega, \varepsilon_0)$ in free space and the complex permittivity of the in vivo surrounding medium by the relation:

$$Z_{ANT}(\omega, \hat{\varepsilon}) = \sqrt{\frac{\varepsilon_0}{\hat{\varepsilon}}} Z_{ANT}\left(\frac{\hat{\varepsilon}}{\varepsilon_0}\omega, \varepsilon_0\right) \quad \text{(eq 5)}$$

Thus, by comparison of the reflected electrical signal RS with the incident electrical signal IS, it is possible to successively determine the reflection coefficient $S_{11}$, the complex impedance $Z_{ANT}(\omega, \hat{\varepsilon})$ of the antenna and the complex permittivity of the surrounding in vivo medium.

According to one or more embodiments, the rate of impedance mismatch between the radio antenna 103 and the radiofrequency 101 is limited so as to guarantee an acceptable level of performance of the radio antenna 103 in data transmission at the frequency of operation f$_0$. For example, the configuration of the radio antenna will be chosen so that the reflection coefficient |$S_{11}$| remains, at the operating frequency of the radio antenna 103, less than −3 dB in the biological environment or environments in which the radio antenna is intended to be used. The operating frequency f$_0$ of the radio antenna 103 corresponds to the frequency of the electromagnetic wave emitted by the radio antenna.

According to one or more embodiments, the microcontroller comprises an electrical signal analysis unit 111 configured to calculate the complex impedance $Z_{ANT}$ of the radio antenna 103, the reflection coefficient $S_{11}$ and/or values of the electromagnetic or physiological properties of the surrounding biological medium 110 from the reflected electrical signal RS.

According to one or more embodiments, the microcontroller 101 comprises an electrical signal generation unit 112 configured to generate the electrical setpoint signal CS. According to one or more embodiments, the microcontroller comprises a data processing unit 113. The data processing unit 113 is for example configured for, on the basis of parameter values (complex impedance $Z_{ANT}$ of the radio antenna 103, reflection coefficient $S_{11}$, electromagnetic properties and/or physiological properties of the biological medium 110) calculated by the electrical signal analysis unit 111, determining the setpoint signal CS to be transmitted by the electrical signal generation unit 112.

According to one or more embodiments, the microcontroller 101 (or the external device) is configured to determine the complex impedance $Z_{ANT}$ of the radio antenna 103 at the operating frequency determined from the reflection coefficient $S_{11}$ and/or the complex intensity of the incident electrical signal IS and of the reflected electrical signal RS on the basis of equations (eq3) and (eq4).

According to one or more embodiments, the microcontroller 101 (or the external device) is configured to determine EM properties (in particular, permittivity ε and conductivity σ) of the surrounding biological medium from the complex impedance $Z_{ANT}$ and/or the coefficient of Reflection $S_{11}$. Such a determination depends on the physical configuration of the radio antenna and can be carried out from a mathematical model linking the complex impedance in free space to the complex impedance in vivo and to the EM properties (in particular, permittivity ε and conductivity σ). Such a determination can be made in particular on the basis of the equation (eq2).

Analytical models exist for simple radio antennas in the form of short monopole probes (see the document Burdette et al. cited above) or coaxial probes (see for example the document entitled "An improved technique for permeattivity measurement using a coaxial probe", Blackham et al., IEEE Transactions on Instrumentation and Measurements, vol. 46, n° 45, pp 1093-1099, October 1997). For more complex radio antennas for which no analytical model is available, a digital model can be generated using the radio antenna in media with known EM properties, so for example to relate values of complex impedance $Z_{ANT}$ of the radio antenna in the medium and/or of the reflection coefficient $S_{11}$ to values of permittivity ε and/or conductivity σ of the medium. Then the radio antenna can be used in environments with unknown EM properties, the values of these properties being determined by interpolation from the values of the digital model, and the complex impedance $Z_{ANT}$ and/or the reflection coefficient $S_{11}$ determined by the microcontroller.

The variation in impedance caused by the surrounding biological medium 110 depends on the thickness and the permittivity of the biocompatible capsule in which the biotelemetry device is encapsulated and which separates the biotelemetry device from the biological medium 110. The higher the thickness (or respectively the permittivity), the lower the sensitivity. As a result, a thinner capsule can detect a finer variation in EM properties, but the range of the radio antenna detuning (or robustness) narrows.

According to one or more embodiments, the radio antenna is configured to operate in biological media having varied EM properties. The radio antenna is for example produced by a microstrip, and isolated from the biological medium by a biocompatible capsule with high permittivity in which this radio antenna is encapsulated. The antenna can also be made of an electrically conductive material (for example, of metal such as copper, aluminum, silver etc. or an alloy). The other embodiments described with reference to FIG. 1 or 2 are also applicable.

Figure 3A:
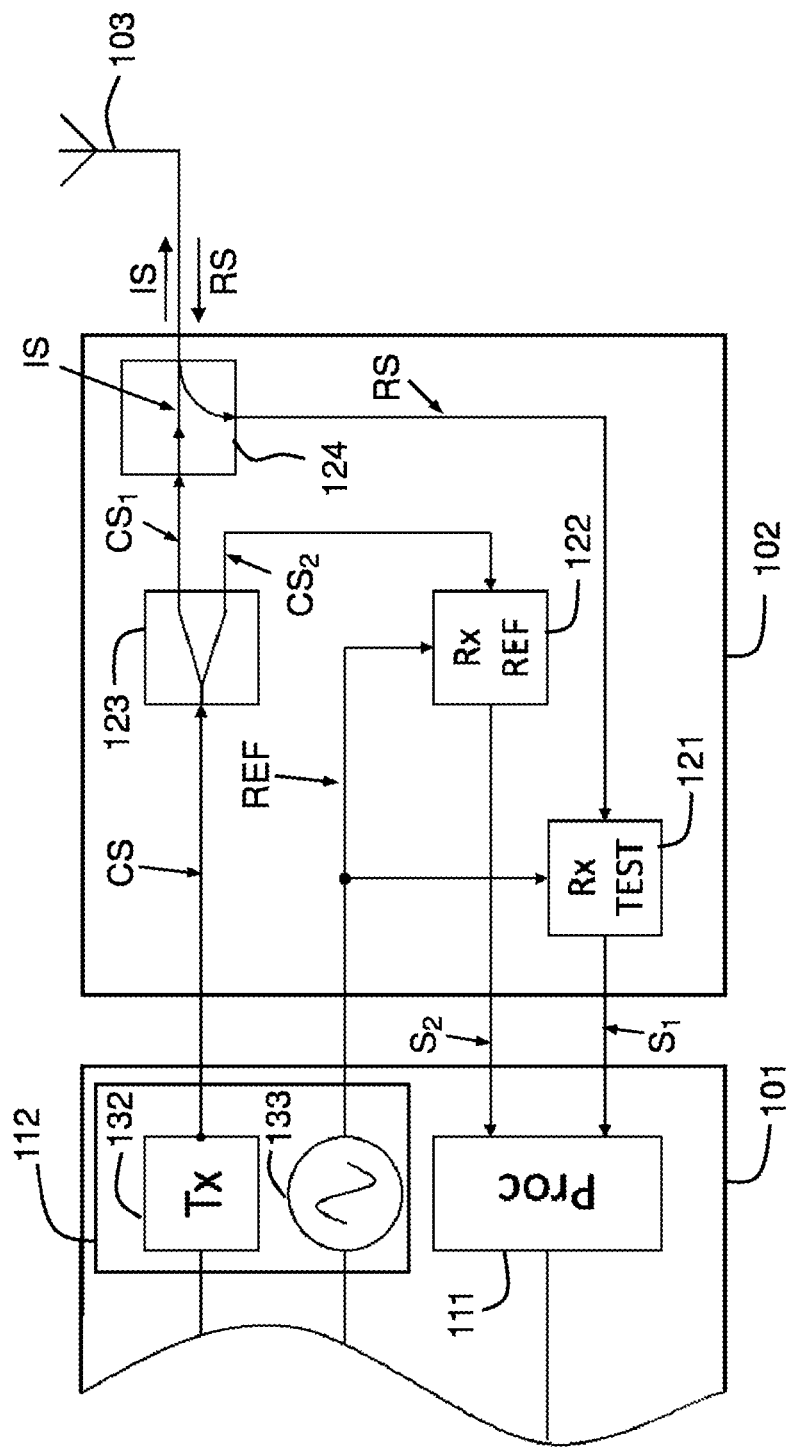

FIG. 3A shows a first example of implantation of the radiofrequency circuit 102 and of the microcontroller 101.

According to one or more embodiments, the unit 112 for generating an electrical signal comprises a subunit 132 for generating the electrical setpoint signal CS and a subunit 133 for generating a reference electrical signal REF. The reference signal is for example a harmonic signal.

According to one or more embodiments, the radiofrequency circuit 102 comprises a power divider 123 configured to pick up a first fraction CS1 of the electrical setpoint signal, pick up a second fraction CS2 of the electrical setpoint signal and generate the incident electrical signal IS from of the first fraction CS1 of the electrical setpoint signal. According to one or more embodiments, the incident electrical signal IS corresponds to the first fraction CS1 of the electrical setpoint signal.

According to one or more embodiments, the radiofrequency circuit 102 comprises an analyzer configured to compare the amplitude and/or the phase of the second fraction CS2 of the electrical setpoint signal with those of the reference signal REF. According to one or more embodiments illustrated by FIG. 3A, this analyzer comprises a directional coupler 124, a test receiver 121 and a reference receiver 122.

According to one or more embodiments, the directional coupler 124 configured to pick up the reflected electrical signal RS by the radio antenna 103.

According to one or more embodiments, the test receiver 121 is configured to compare the reflected electrical signal RS picked up by the directional coupler 124 with the reference signal REF. The first test receiver 121 generates an electrical comparison signal S1 resulting from this comparison. The comparison carried out by the test receiver consists in comparing the amplitude and the phase of the reflected electrical signal RS picked up by the directional coupler 124 with those of the reference signal REF.

According to one or more embodiments, the reference receiver 122 is configured to compare the second fraction CS2 of the electrical setpoint signal with the reference signal REF. The test receiver 121 generates an electrical comparison signal S2 resulting from this comparison. The comparison carried out by the second network consists in comparing the amplitude and the phase of the second fraction CS2 of the electrical setpoint signal with those of the reference signal REF.

According to one or more embodiments, the radiofrequency circuit 102 is configured to pick up a first fraction CS1 of the electrical setpoint signal CS, transmit to the radio antenna a second fraction CS2 of the electrical setpoint signal forming the incident electrical signal IS and pick up the reflected electrical signal RS by the radio antenna, separating the reflected electrical signal RS from the incident electrical signal IS.

According to one or more embodiments, the microcontroller is configured to determine, relative to the first fraction CS1 of the setpoint electrical signal, the reflection coefficient $S_{11}$ corresponding to the fraction of the electrical signal RS reflected by the radio antenna 103. According to one or more embodiments, the electrical signal analysis unit 111 is configured to receive the electrical comparison signals S1 and S2 and to calculate the complex impedance $Z_{ANT}$ of the radio antenna 103, the reflection coefficient $S_{11}$ and/or values of electromagnetic or physiological properties of the surrounding biological medium 110 from the electrical comparison signals S1 and S2.

Figure 3B:
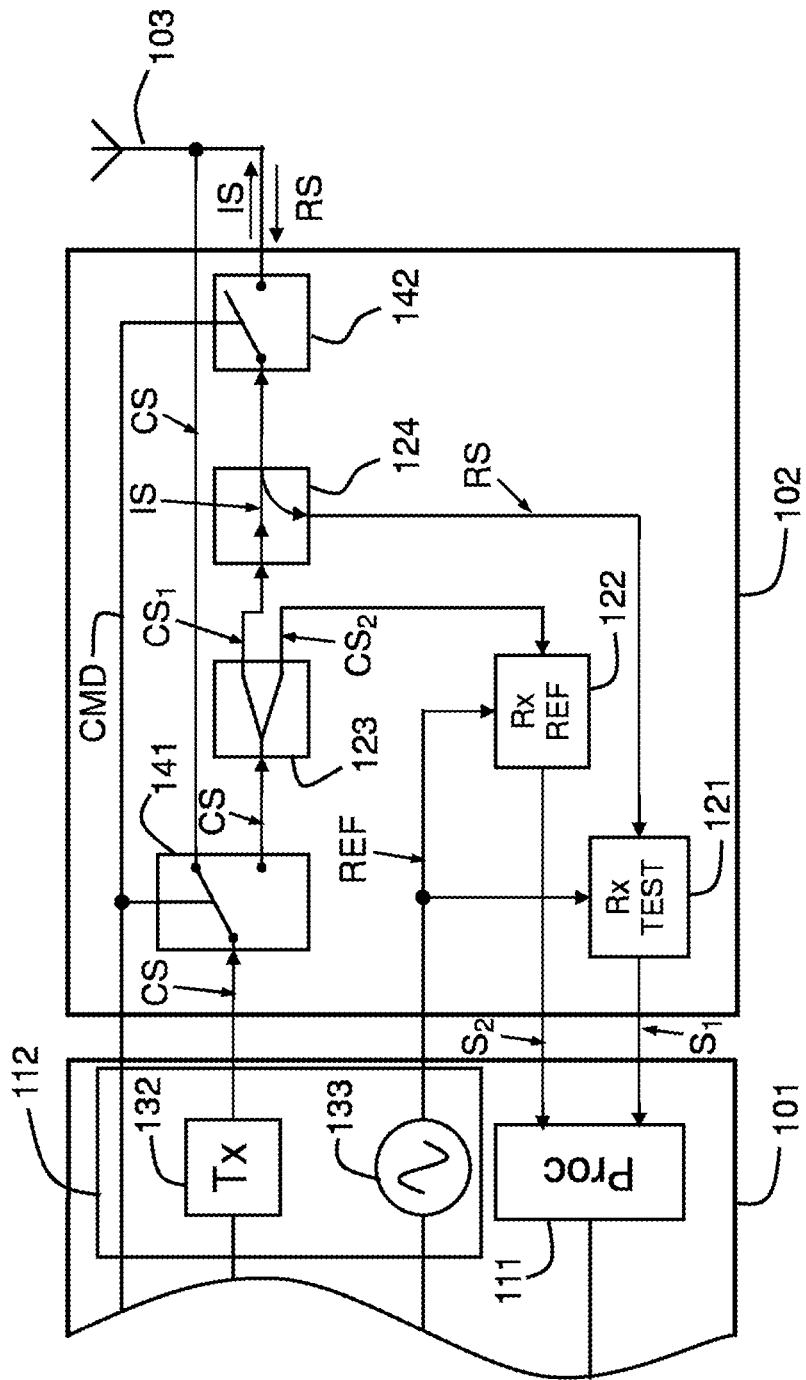

FIG. 3B shows a second example of installation of the radio frequency circuit 102 and of the microcontroller 101. In this second example of implantation of the radiofrequency circuit 102, the elements identical to those of the first example of implantation of the radiofrequency circuit described with reference to FIG. 3A are not described again and bear the same references in FIGS. 3A and 3B.

According to one or more embodiments, the radio frequency circuit 102 further comprises at least one electrical switch 141, 142 configured to switch the radio frequency circuit 102 from a first operating mode to a second operating mode and vice versa. The radio frequency circuit 102 is configured for, in the first operating mode, for picking up the first fraction of the setpoint electrical signal and the fraction of the electric signal reflected by the radio antenna and for generating the incident electric signal from the second fraction of the electrical setpoint signal. The radiofrequency circuit is configured to, in the second operating mode, transmit the entire setpoint electrical signal to the radio antenna and not pick any fraction of the electrical signal reflected by the radio antenna up. It is thus possible to switch from the first operating mode in which values of EM or physiological properties of the surrounding biological medium 110 can be determined from the electrical signal reflected by the radio antenna, to the second operating mode in which the electrical signal RS reflected by the radio antenna 103 is not picked up and no value of EM or physiological properties of the surrounding biological medium 110 can be determined from the electrical signal RS reflected by the radio antenna 103.

In the embodiment shown in FIG. 3B, a first electrical switch 141 is interconnected between the output of the subunit 132 for generating the electrical setpoint signal CS and the input of the power divider 123 and a second electrical switch 141 is interconnected between the output of the directional coupler 124 and the radio antenna 103.

In at least one embodiment, which can be combined with the embodiments described with reference to FIG. 1, 2, 3A or 3B, the biotelemetry device comprises an impedance matching circuit 150 (not shown), interconnected between the radio antenna 103 and the radio frequency circuit 102. The impedance matching circuit 150 is configured to implement impedance matching. This impedance adaptation is for example configured as a function of the reflection coefficient $S_{11}$. Thus, it is possible to dynamically adjust the reflection coefficient $S_{11}$ actually obtained and the properties (in particular amplitude, phase) of the reflected electrical signal RS, for example depending on the intended use for the biotelemetry device 100 at a given time or so as to obtain a given level of quality for the reflected electrical signal RS or the electromagnetic wave EMS emitted by the antenna or to increase the range of the antenna.

Figure 4A:
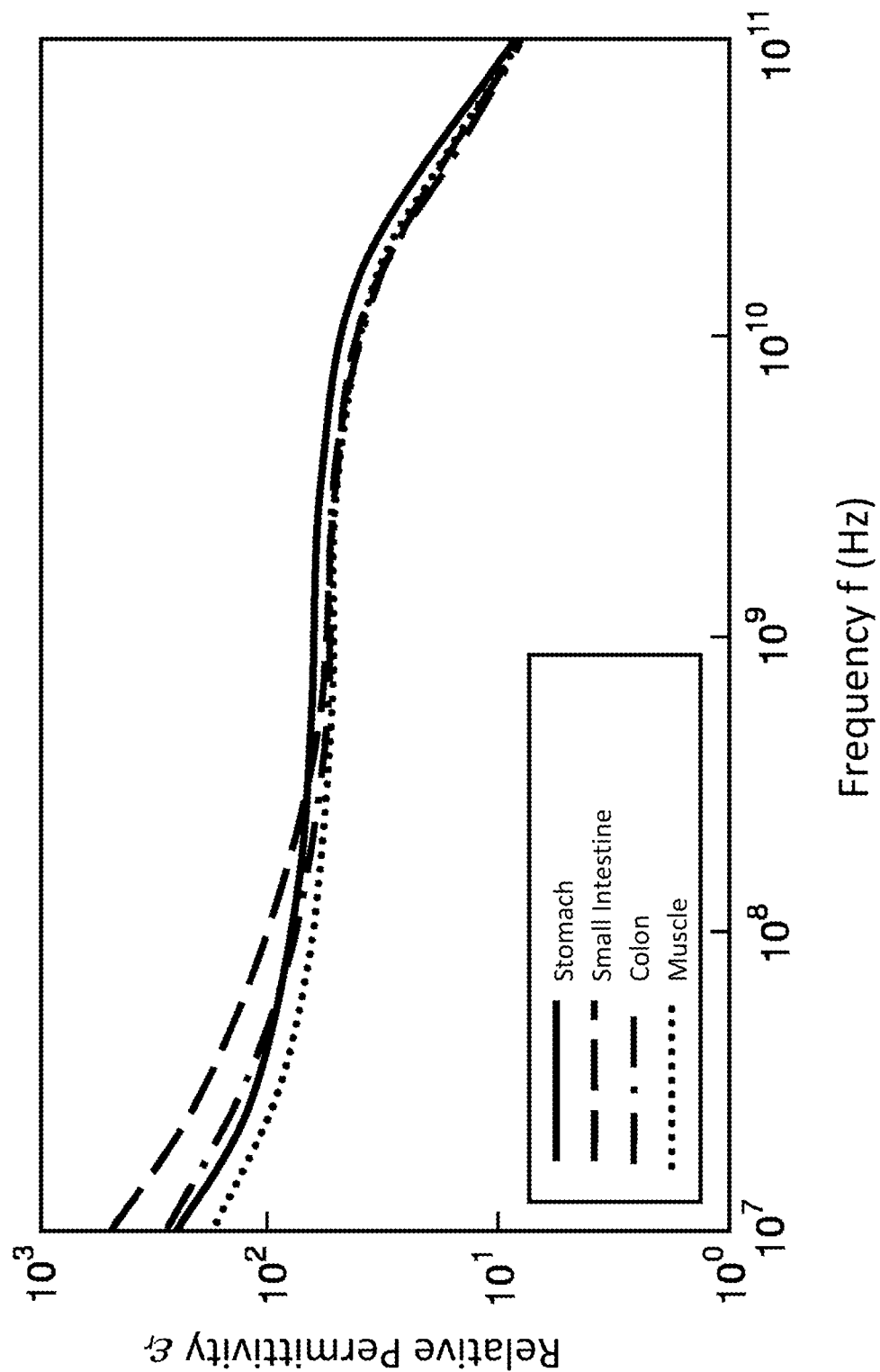
FIGS. 4A and 4B illustrate the relationship between the electromagnetic properties of a medium and the operating frequency of a biotelemetry device according to an exemplary embodiment.

FIG. 4A shows the curves of variation of the relative permittivity of different organs as a function of the operating frequency: stomach, small intestine, colon and muscle. The values of the esophagus are identical to those of the stomach. It is observed that, for a given operating frequency, the relative permittivity depends on the organ, the differences remaining appreciable below 1 GHz.

Figure 4B:
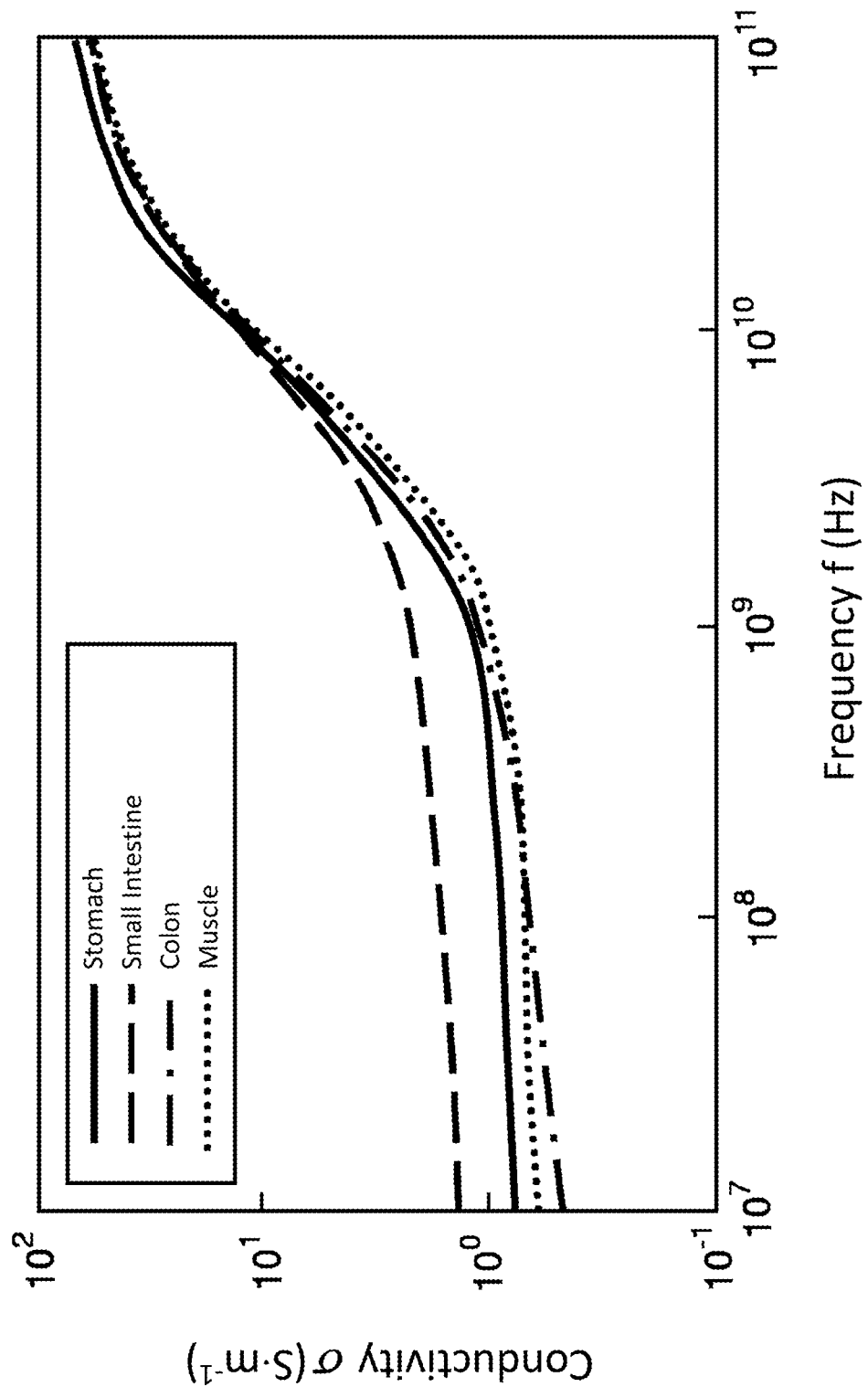

FIG. 4B shows the variation curves of the conductivity of different organs as a function of the operating frequency: stomach, small intestine, colon and muscle. The values of the esophagus are identical to those of the stomach. It is also observed that, for a given operating frequency, the relative permittivity depends on the organ, the differences remaining appreciable below 10 GHz.

On the basis of the curves of FIGS. 4A and 4B, it is therefore possible to determine a range of operating frequency which can be used according to the intended applications. For example, using an operating frequency at 434 MHz (ISM band, industrial, scientific and medical), the differences in relative permittivity and conductivity values between the organs are large enough to be able to be detected, while having a sufficiently high frequency to allow a significant transmission rate and good diffusion through the human body of EM waves.

Thus, in an example of application of the biotelemetry device according to the present description, it is possible to determine, for example in the microcontroller or in an external device communicating with the biotelemetry device 100, on the basis of variation curves of the EM properties in different organs such as those of FIGS. 4A and 4B, the organ of the human body in which the biotelemetry device is located at a given instant as a function of the EM properties of the biological medium 110 determined by the microcontroller 101 from the complex impedance $Z_{ANT}$ and/or from the reflection coefficient $S_{11}$. Other information can then be deduced, such as for example a gastrointestinal transit time.

In an example application where the biotelemetry device is configured to perform an endoscopy of a specific organ or a specific section of the gastrointestinal tract (for example, of the small intestine), it is possible to activate the endoscopy camera only when the biotelemetry device reaches this specific organ/section and thus save the battery of the biotelemetry device, and/or better use this battery in order to improve image acquisition (for example, the number of images acquired per second) by the endoscopy camera.

In an example of application where the biotelemetry device is configured to deliver a drug to a specific organ or a specific section of the gastrointestinal tract, the drug can be released automatically when the EM properties of the biological medium 110 correspond to the EM properties of this specific organ or respectively this specific section.

The table in FIG. 5 gives some example values of relative permittivity and conductivity for the stomach, small intestine, colon and muscle at some example operating frequency values. We observe that beyond 2.4 GHz, the values for the small intestine and the colon are very close: it is therefore difficult to distinguish these two organs by working at such frequencies.

The biotelemetry device has many possibilities of application, whether in the medical or non-medical field, for example, for civil engineering, agriculture, food processing, etc.

The invention claimed is:

1. Biotelemetry device for use in a biological medium, wherein the biotelemetry device comprises:
   a microcontroller configured to generate an electrical setpoint signal;
   a radio antenna configured to transmit an electromagnetic wave to an external device by converting an incident electrical signal;
   a radio frequency circuit, interconnected between the microcontroller and the radio antenna,
   the radio antenna being configured to, when the biotelemetry device is placed in the biological medium, be impedance mismatched with respect to the radio frequency circuit so as to generate a reflected electrical signal by reflection of a fraction of the incident electrical signal, wherein the generation of the reflected electrical signal occurs at the same time the radio antenna emits the electromagnetic wave to the external device;
   in which the radio frequency circuit is configured to, in a first operating mode, pick up a first fraction of the electrical setpoint signal, transmit to the radio antenna a second fraction of the electrical setpoint signal and pick up the reflected electrical signal, wherein the second fraction of the electrical setpoint signal forms the incident electrical signal;
   in which the microcontroller is configured to determine a reflection coefficient based on the first fraction of the electrical setpoint signal and the reflected electrical signal.

2. The biotelemetry device according to claim 1, in which the microcontroller is further configured to obtain a first electrical comparison signal resulting from a comparison between a reference signal and the first fraction of the electrical setpoint signal and to obtain a second electrical comparison signal resulting from a comparison between the reference signal and the reflected electrical signal.

3. The biotelemetry device according to claim 2, wherein the microcontroller is further configured to determine the reflection coefficient from the first electrical comparison signal and the second electrical comparison signal.

4. The biotelemetry device according to claim 3, in which the microcontroller is further configured to determine an electromagnetic parameter of the biological medium from an amplitude and a phase of the first electrical comparison signal and an amplitude and a phase of the second electrical comparison signal.

5. The biotelemetry device according to claim 1, in which the radio frequency circuit comprises a power divider configured to pick up the first fraction of the electrical setpoint signal and generate the incident electrical signal.

6. The biotelemetry device according to claim 1, in which the radio frequency circuit comprises a directional coupler configured to pick up the reflected electrical signal.

7. The biotelemetry device according to claim 1, in which the radio frequency circuit comprises a reference receiver configured to compare a reference signal and the first fraction of the electrical setpoint signal and a test receiver configured to compare the reference signal and the reflected electrical signal.

8. The biotelemetry device according to claim 1, in which the radio frequency circuit further comprises at least one switch configured to switch the radio frequency circuit from the first operating mode to a second operating mode and vice versa,
the radio frequency circuit being configured to, in the second operating mode, transmit an entirety of the electrical setpoint signal to the radio antenna and pick up no fraction of the electrical signal reflected by the radio antenna.

9. The biotelemetry device according to claim 1, comprising an impedance matching circuit, interconnected between the microcontroller and the radio frequency circuit and configured to implement an impedance matching based on the determined reflection coefficient.

10. The biotelemetry device according to claim 1, in which the reflection coefficient is, at an operating frequency of the radio antenna, less than −3 dB.

11. The biotelemetry device according to claim 1, in which the microcontroller is further configured to determine, from the reflection coefficient, a complex impedance of the antenna, when the antenna is in the biological medium, at an operating frequency of the radio antenna.

12. The biotelemetry device according to claim 11, wherein the microcontroller is further configured to determine one or more electromagnetic properties of the biological medium from a model linking the complex impedance of the antenna in free space to the complex impedance of the antenna in the biological medium and the one or more electromagnetic properties.

13. A system comprising a biotelemetry device according to claim 1 and an external device configured to receive electromagnetic waves emitted by the antenna of the biotelemetry device and/or send commands to the biotelemetry device via a radio connection.

14. The system of claim 13 wherein the external device is further configured to determine from the reflection coefficient a complex impedance of the radio antenna, when the radio antenna is in the biological medium, at an operating frequency of the radio antenna and to determine electromagnetic properties of the biological medium from a model linking the complex impedance of the antenna in free space to the complex impedance of the antenna in the biological medium and the electromagnetic properties.

15. Biotelemetry measurement method, the method being intended to be implemented by means of a biotelemetry device placed in a surrounding biological medium, the method comprising:
a generation of an electrical setpoint signal by a microcontroller of the biotelemetry device;
an emission, by a radio antenna of the biotelemetry device, of an electromagnetic wave to an external device by conversion of an incident electric signal;
a generation of a reflected electrical signal, the reflected electrical signal resulting from an impedance mismatch of the radio antenna with respect to a radio frequency circuit when the biotelemetry device is placed in the biological medium and being generated by reflection by the radio antenna of a fraction of the incident electric signal concomitantly with the emission of the electromagnetic wave, wherein the radio frequency circuit is interconnected between the microcontroller and the radio antenna;
a picking up, by the radio frequency circuit of the biotelemetry device of a first fraction of the electrical setpoint signal and of the electrical signal reflected by the radio antenna;
a transmission to the radio antenna of a second fraction of the setpoint electrical signal, wherein the second fraction of the setpoint electrical signal forms the incident electric signal;
a determination, by the microcontroller, of a reflection coefficient based on the first fraction of the electrical setpoint signal and the reflected electrical signal.

* * * * *